United States Patent [19]

Schmukler

[11] Patent Number: 5,571,156
[45] Date of Patent: Nov. 5, 1996

[54] SWITCHED IMPLANTABLE ELECTRICAL STIMULATOR LEADS

[75] Inventor: Robert E. Schmukler, Rockville, Md.

[73] Assignee: The United States of America as represented by the Department of Health and Human Services, Washington, D.C.

[21] Appl. No.: 263,312

[22] Filed: Jun. 21, 1994

[51] Int. Cl.⁶ ........................................ A61N 1/04
[52] U.S. Cl. ................................................ 607/116
[58] Field of Search ........................ 607/115, 119, 607/122–124, 129, 37, 38, 5, 9, 13, 27–29, 36–37, 116, 150; 128/642

[56] References Cited

U.S. PATENT DOCUMENTS

| 1,074,146 | 9/1913 | Wappler | 607/150 |
|---|---|---|---|
| 3,224,447 | 12/1965 | Becker et al. | 607/5 |
| 3,706,313 | 12/1972 | Milani et al. | 607/5 |
| 4,141,367 | 2/1979 | Ferreira . | |
| 4,579,119 | 4/1986 | Callaghan | 607/13 |
| 4,628,934 | 12/1986 | Pohndorf et al. | 607/27 |
| 4,658,831 | 4/1987 | Reinhard et al. . | |
| 4,686,990 | 8/1987 | Moberg . | |
| 4,694,830 | 9/1987 | Lekholm . | |
| 4,705,042 | 11/1987 | Giurtino . | |
| 4,715,381 | 12/1987 | Moberg . | |
| 4,819,657 | 4/1989 | Karft et al. . | |
| 4,964,407 | 10/1990 | Baker, Jr. et al. . | |
| 5,137,021 | 8/1992 | Wayne et al. . | |
| 5,336,253 | 8/1994 | Gordon et al. | 607/122 |

Primary Examiner—William E. Kamm
Attorney, Agent, or Firm—Townsend and Townsend and Crew LLP

[57] ABSTRACT

A pacemaker includes apparatus and method for testing the integrity of an insulated pacemaker lead to detect lead degradation at an early stage and warn the user. An electronic switch is placed between two ends of an insulated pacemaker lead that couples a pacemaker housing to the heart of a pacemaker user. The pacemaker electronics circuit asserts a control signal to the switch, opening the switch and interrupting the continuity of the insulated pacemaker lead. After the switch interrupts continuity of the lead, an onboard lead integrity tester tests for insulation leakage of the insulated pacemaker leads by measuring a quality factor, Q, of the insulated lead.

6 Claims, 2 Drawing Sheets

SWITCHED IMPLANTABLE ELECTRICAL STIMULATOR LEADS

BACKGROUND OF THE INVENTION

The present invention relates generally to electrical stimulator leads. More specifically, the present invention relates to a method and apparatus for in situ testing of an integrity of electrical stimulator leads used in pacemakers.

Pacemakers include a housing containing electronic control and operational circuitry and either one or two electrical stimulator leads coupling the circuitry to a patient's heart. Two leads provide for a return path for electrical signals while a patient's body provides the return path when only one lead is used.

Installing a pacemaker in a patient requires a couple of surgical procedures. A first procedure implants the electrical stimulator leads directly into the heart. Ends of the leads opposite the electrodes inserted into the heart are brought near the surface of the skin, typically somewhere near the chest cavity. During a second installation operation, a surgeon implants the pacemaker housing near the skin surface of the patient and attaches the free ends of the stimulator leads. The reason for installing the pacemaker near the skin's surface is to permit servicing, or replacement, of the pacemaker on an outpatient basis. The stimulator leads, on the other hand, are permanently installed.

Pacemakers include many features to perform self-checking and testing of the circuitry to ensure proper operation. The electrical stimulator leads can fail as well, but they are not removed or serviced. Wires from the implanted electrodes are cut, leaving the electrode in the heart, and a new stimulator lead is implanted. The electrical stimulator leads typically consist of wires encased in a protective sheathing, insulating the wires. Due to the severity of the procedure to add new electrical stimulator leads, the leads are designed to last a long time. Unfortunately, in the prior art, there is no reliable way to monitor or judge when a lead is beginning to fail. Until the performance of the pacemaker system degrades significantly or fails, minor defects or failures that have developed over the life of the leads are undetectable.

SUMMARY OF THE INVENTION

The present invention provides apparatus and method for testing the integrity of an insulated electrical stimulator lead to detect lead degradation at an early stage.

A pacemaker housing, including electronic circuits for generating pacemaker signals to the heart, is installed just beneath the skin surface of a pacemaker user. A pair of insulated pacemaker leads couple the pacemaker electronics to the heart, with an electrode implanted in the heart at one end of each lead. An electronic switch couples two ends of the first insulated pacemaker lead together.

A third insulated pacemaker lead couples the pacemaker electronics to the electronic switch. The pacemaker electronics assert a control signal via the third lead to the electronic switch, opening the switch and interrupting the continuity of the first lead. Once the continuity has been interrupted, a lead integrity tester included in the pacemaker housing tests the first and second leads for insulation leakage. The preferred embodiment measures a quality factor, Q, of the insulated leads to test lead integrity.

A second preferred embodiment of the invention includes a second electronic switch that couples the first lead to the second lead. A fourth insulated pacemaker lead couples the pacemaker electronics to the second switch. The pacemaker electronics assert a control signal via the fourth lead to the second switch, closing the switch in order to establish electrical continuity between first and second leads. Once the switch has established electrical continuity, a tester included in the pacemaker housing determines the impedance between the two implanted lead electrodes.

Reference to the remaining portions of the specifications, including the figures and claims, will realize other features, advantages and modifications to the present invention.

DESCRIPTION OF THE PREFERRED EMBODIMENT

Figure 1:
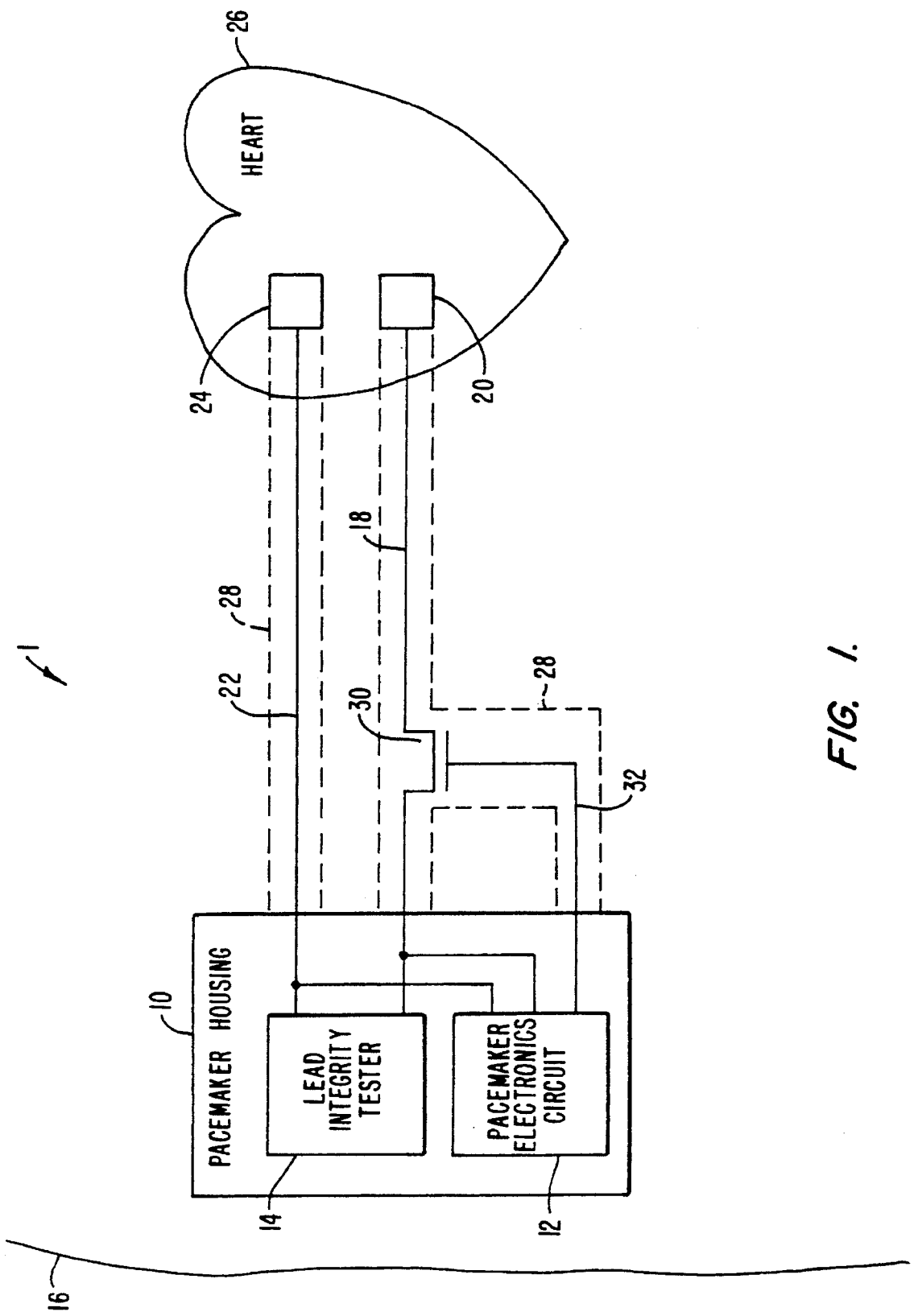
FIG. 1 is an illustration of a heart pacemaker 1 having a capability to test an integrity of insulated pacemaker leads.

FIG. 1 is an illustration of a heart pacemaker 1 having a capability to test an integrity of an insulated pacemaker lead. Pacemaker 1 includes a housing 10, a pacemaker electronics circuit 12 and a lead integrity tester 14. Housing 10 is placed just beneath a skin surface 16 of a pacemaker user.

A first insulated lead 18 couples pacemaker electronics circuit 12 to a first electrode 20. Similarly, a second insulated lead 22 couples pacemaker electronics circuit 12 to a second electrode 24. First electrode 20 and second electrode 24 are implanted in a heart 26 of the pacemaker user. An insulating layer 28 covers each lead.

As well known, standard bipolar pacemaker leads, such as lead 18 and lead 22, are coaxial. One conductor (the inner lead) is surrounded by an insulating layer, that is in turn surrounded by the second conducting layer (the outer lead), surrounded in turn by another insulating layer. In most applications, the outer lead terminates in a ring electrode. The inner lead with its insulating layer extends beyond the ring electrode. Some distance past the ring electrode, the insulating layer surrounding the inner conductor ends, leaving the inner conductor exposed. The end of the inner conductor is generally semi-hemispherical and forms the tip electrode. When implanted, the tip electrode extends into the heart chambers and the ring electrode provides an electrical return path.

An electronic switch 30 is coupled between two ends of first insulated lead 18. In the preferred embodiment, electronic switch 30 includes a field effect transistor configured to be normally closed, but other implementations as well known are possible. A preferred position for switch 30 locates itself as close as possible to the tip electrode (electrode 20). Switch 30 could employ surface mount technology immediately behind electrode 20, with electrode 20 hollowed out to help protect switch 30. A third insulated lead 32 couples pacemaker electronics circuit 12 to switch 30. An insulating layer 28 also covers third lead 32.

In operation, switch 30 is closed and electronics circuit 12 provides pacemaker signals to heart 26 via first insulated lead 18. For testing lead degradation, electronics circuit 12 asserts a control signal via third lead 32 to open switch 30 and interrupt the continuity of first insulated lead 18. After switch 30 interrupts continuity, lead integrity tester 14 tests first insulated lead 18 and second insulated lead 22 for insulation leakage. In the preferred embodiment, integrity tester 14 measures a quality factor, Q, of the insulated leads. Measurement of the quality factor is well known and will not be further described herein. According to the present invention, it would also be possible to conduct other tests using electronic switch 30 to monitor the condition of the leads.

Figure 2:
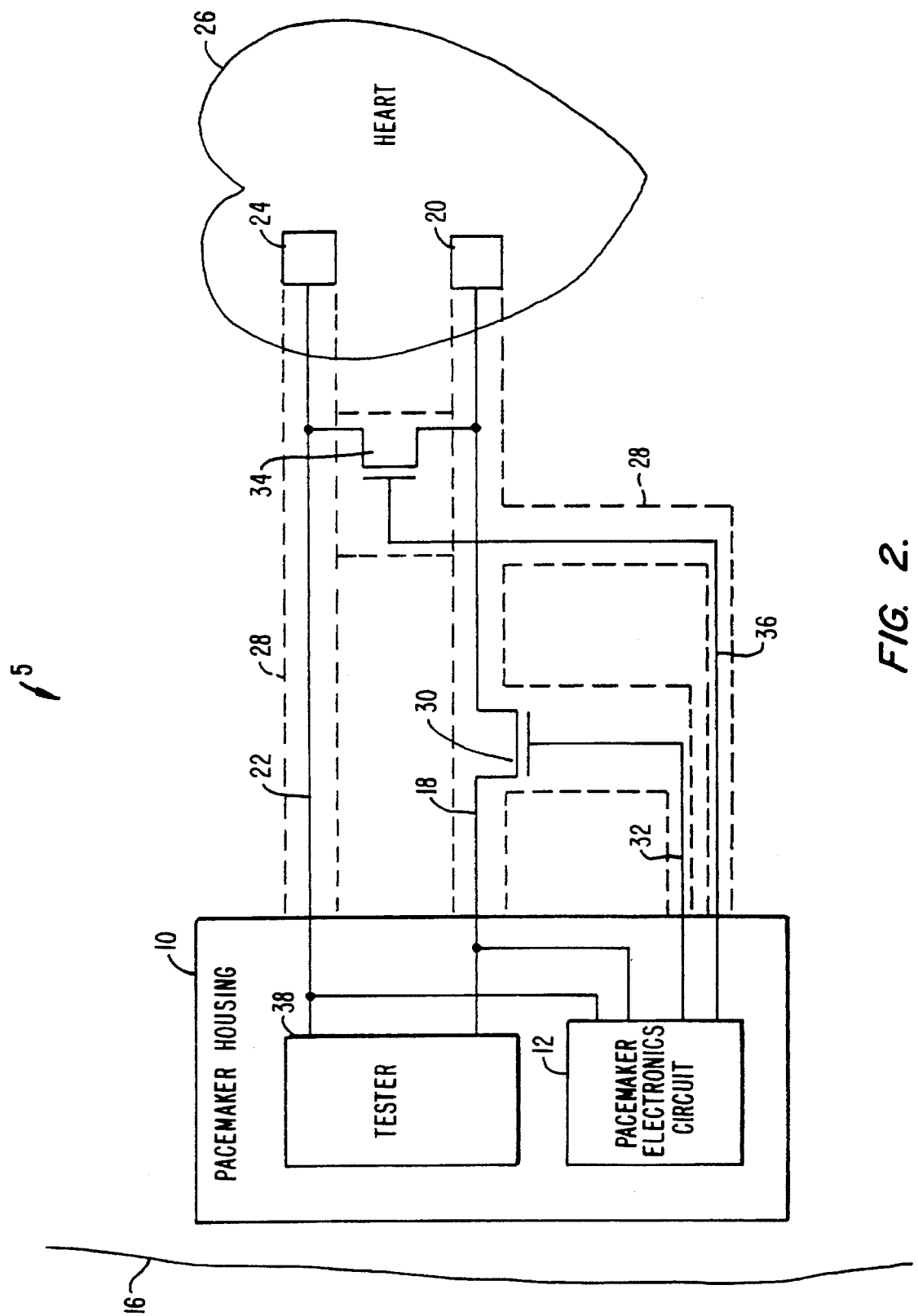
FIG. 2 is an illustration of a heart pacemaker 5 having a capability to test an impedance between implanted lead electrodes.

FIG. 2 is an illustration of a heart pacemaker 5 having a capability to test the impedance between implanted electrodes. Similarly numbered items correspond to previously referenced elements. In addition to switch 30, pacemaker 5 includes a second electronic switch 34, a fourth insulated pacemaker lead 36 and a tester 38. In the preferred embodiment, electronic switch 34 is positioned as close as possible to the ring electrode, and is a normally open switch. Insulating layer 28 covers second switch 34 and fourth lead 36.

Second electronic switch 34 couples first lead 18 to second lead 22, at a point just before where first lead 18 is coupled to first electrode 20 and where second lead 22 is coupled to second electrode 24. Electronic switch 34 includes a field effect transistor, but other implementations as well known are possible. Fourth insulated pacemaker lead 36 couples pacemaker electronics circuit 12 to second switch 34.

In operation, tester 38 initiates an impedance test of an open switch electrical path defined by lead 18, electrode 20, tissue of heart 26, electrode 24, and lead 22. Impedance testing is well known and may be implemented in many different forms. A typical impedance for the open switch electrical path is about 400–500Ω. If the open switch impedance falls to about 250Ω, then a degradation of the lead insulation is indicated.

Thereafter, tester closes electronic switch 34 and measures an impedance of a closed switch electrical path through lead 18, electronic switch 34 and lead 22. Typical impedance values for the impedance of the closed switch path using conventional electrode leads should be about 100Ω. From the difference between the open switch impedance and the closed switch path impedance, information relating to condition of the ring and tip electrodes, as well as condition of the leads themselves may be determined.

Failure of the lead insulation can lead to different problems, including: creation of a leakage pathway that takes pacing energy away from the pacing path (the open switch path), or lead degradation that increases the impedance of a lead to degrade performance. Both of the problems can create a situation such that there is not enough energy to properly stimulate the heart tissue. Any conventional method of relaying the data from the tester to a physician can be used with the present invention. Details regarding conveying the data from the tester to the physician will not be described further herein.

The present invention provides a simple, efficient solution to the problems of early detection of degradation of an insulated pacemaker lead and degradation of an implanted electrode. While the above is a complete description of the preferred embodiments of the invention, various alternatives, modifications, and equivalents may be used.

For example, other switches other than an FET may be substituted, and the invention is adaptable to operate with monopolar pacemakers having a single pacing lead. With a monopolar-type pacemaker, switch 30 could be installed adjacent to the return electrode provided on the side of the pacemaker housing.

The present invention is not limited to pacemakers or pacemaker leads. Other applications require implantation of electrical stimulator leads and it may be desirable to perform in situ testing of the leads using the present invention. Some of these applications include neuro-muscular stimulators, implanted defibrillators, cochlear implants, for example. Therefore, the above description should not be taken as limiting the scope of the invention which is defined by the appended claims.

What is claimed is:

1. A lead for use with an electronic controller, comprising:
   a first conductor including a first electrode adapted for implantation into tissue, a first end of said first conductor for coupling to the electronic controller and a second end of said first conductor coupled to said first electrode; and
   a first electronic switch coupled between said ends of said first conductor and integrated into said first electrode wherein said first switch includes a first state and a second state with said first state providing electrical continuity between the electronic controller and said tissue and said second state interrupting electrical continuity between the electronic controller and said tissue.

2. The lead of claim 1 further comprising:
   a second conductor including a second electrode adapted for implantation into said tissue, a first end of said second conductor for coupling to the electronic controller and a second end of said second conductor coupled to said second electrode;
   an insulating layer separating said first and said second conductor; and
   a second electronic switch, said second electronic switch coupled between said first conductor and said second conductor, wherein said second electronic switch includes a first state and a second state with said first state providing electrical continuity between said conductors and said second state interrupting electrical continuity between conductors.

3. The lead of claim 2, wherein said first electronic switch is responsive to a first control signal for controlling said states of said first electronic switch and wherein said second electronic switch is responsive to a second control signal for controlling said states of said second electronic switch, the lead further comprising:
   means for providing said first control signal to said first electronic switch; and
   means for providing said second control signal to said second electronic switch.

4. The lead of claim 3 wherein said providing means includes means for controlling said states of said first electronic switch and said second electronic switch independent of signals on said conductors.

5. A lead for use with an electronic controller, comprising:
   a first conductor including a first electrode adapted for implantation into tissue, a first end of said first conductor for coupling to the electronic controller and a second end of said first conductor coupled to said first electrode; and
   a first electronic switch, coupled between said ends of said first conductor and integrated into said first electrode, wherein said first switch includes a first state and a second state with said first state providing electrical continuity between the electronic controller and said tissue and said second state interrupting electrical continuity between the electronic controller and said tissue;
   wherein said first electronic switch is responsive to a control signal for controlling said states, the lead further comprising means for providing said control signal to said first electronic switch.

6. The lead of claim 5 wherein said providing means includes means for controlling said states of said first electronic switch independent of signals on said first conductor.

* * * * *